(12) United States Patent
Ruetschi et al.

(10) Patent No.: US 12,009,074 B2
(45) Date of Patent: Jun. 11, 2024

(54) SYSTEM AND METHOD FOR AUGMENTATING VIDEO DATA

(71) Applicant: Unify Patente GmbH & Co. KG, Munich (DE)

(72) Inventors: Johannes Ruetschi, Boca Raton, FL (US); Rodrigo Pastro, Lake Worth, FL (US); Christian Garbin, Boca Raton, FL (US)

(73) Assignee: Unify Patente GmbH & Co. KG, Munich (DE)

( * ) Notice: Subject to any disclaimer, the term of this patent is extended or adjusted under 35 U.S.C. 154(b) by 351 days.

(21) Appl. No.: 17/443,524

(22) Filed: Jul. 27, 2021

(65) Prior Publication Data

US 2022/0238194 A1 Jul. 28, 2022

Related U.S. Application Data

(60) Provisional application No. 63/141,719, filed on Jan. 26, 2021.

(51) Int. Cl.
*G16H 10/60* (2018.01)
*G06F 3/048* (2013.01)
*G16H 80/00* (2018.01)

(52) U.S. Cl.
CPC ............ *G16H 10/60* (2018.01); *G06F 3/048* (2013.01); *G16H 80/00* (2018.01)

(58) Field of Classification Search
None
See application file for complete search history.

(56) References Cited

U.S. PATENT DOCUMENTS

| | | |
|---|---|---|
| 2013/0246084 A1 | 9/2013 | Parmanto et al. |
| 2014/0075295 A1* | 3/2014 | Xu .......................... G06F 40/58 715/243 |
| 2014/0240444 A1 | 8/2014 | Szymczyk et al. |
| 2015/0294079 A1 | 10/2015 | Bergougnan |
| 2017/0011192 A1* | 1/2017 | Arshad ................. G16H 40/20 |
| 2017/0323485 A1 | 11/2017 | Samec et al. |
| 2018/0226158 A1 | 8/2018 | Fish et al. |
| 2018/0360295 A1* | 12/2018 | Boucher ................ G16H 30/20 |
| 2021/0055537 A1* | 2/2021 | Komp .................... G16H 50/50 |

* cited by examiner

*Primary Examiner* — Thu N Nguyen
(74) *Attorney, Agent, or Firm* — Buchanan Ingersoll & Rooney PC

(57) ABSTRACT

A communication apparatus and method for augmenting at least one data stream (e.g. a video stream) with data obtained from at least one computer device can facilitate the generation of a user interface that can provide an enhancement in telecommunication services. For example, in some embodiments a video stream from a patient device that is involved in a telecommunication communication session that also include at least one medical care device can be augmented to include data from the patient's health records stored in a computer device such that a graphical user interface displayed on the medical care device can include medical record indicia positioned over an image of the patient to indicate different health records related to parts of the patient's body being displayed. The indicia can provide information related to the age of the medical data and/or other aspects of a medical record indicated by the indicia.

17 Claims, 4 Drawing Sheets

SYSTEM AND METHOD FOR AUGMENTATING VIDEO DATA

CROSS-REFERENCE TO RELATED APPLICATIONS

The present application claims priority to U.S. Provisional Patent Application No. 63/141,719, which was filed on Jan. 26, 2021. The entirety of this provisional patent application is incorporated by reference herein.

FIELD

The present innovation relates to methods for augmentation telecommunication data to provide a user interface that is displayable via at least one telecommunication terminal device (e.g. a smart phone, a laptop computer, a tablet computer device, etc.) that can facilitate medical services that can be provided via a telecommunications system. Apparatuses and systems configured to utilize embodiments of such methods are also provided.

BACKGROUND

There has been an increase in telephonic and video call communications. For example, there is an increase in healthcare providers providing telehealth consultation services in which a doctor or nurse practitioner may communicate with a patient to diagnose a health issue the patient may be experiencing. Examples of telehealth systems and processes can be appreciated from U.S. Pat. App. Pub. Nos. 2018/0360295, 2018/0226158, 2017/0011192, 2017/0323485, 2015/0294079, 2014/0240444, and 2013/0246084.

SUMMARY

Over time, people can accumulate a trail of medical records that can be relevant to treatment of other health conditions these people may experience. These patients can receive care from different doctors or other care providers that may be employed by the same health care provider or may be employed by different health care providers. Such health care providing personnel may not be aware of the patient's past history or have been able to review a file of the patient to understand relevant patient history prior to a particular appointment. Patient history can be relatively long and complex and it can be difficult, if not impossible, for a health care provider such as a doctor, surgeon, nurse practitioner, or nurse, to recall the patient's history relevant to a particular health issue that may be discussed or reviewed in a particular appointment. Search functionality of the health care provider's electronic health record (EHR) system can also fail to help a care provider find relevant records related to the patient's medical history that can be related to the health issue being discussed in a particular appointment. Apparatuses and methods are provided herein that can help address these types of issues to improve the health care provider's ability to provide high quality health care services that takes into account the patient's relevant past medical history. Embodiments can be adapted for utilization in telehealth settings in which the appointment between the patient and care provider occurs via a communication session that is formed between the patient's communication deice and the care provider's communication device (e.g. patient laptop computer and doctor laptop computer, patient smart phone and care provider tablet computer device, patient laptop computer and care provider smart phone, etc.).

Some embodiments can be configured to augment data streams received from the patient's device so that indicia related to health records of different patient body parts to be displayed to the care provider are visible so the care provider can be aware of relevant past medical history events related to the patient at the time of the appointment and review those records in real time during the communication session while the patient may be interacting with the care provider via the communication session. Embodiments can permit a care provider to be quickly aware of relevant past medical history without having to independently search for relevant medical history documents or review those documents before an appointment. Moreover, the data can be communicated via a user interface to permit the care provider to be aware of and review pertinent record data while maintaining a position that indicates to the patient that the care provider is paying attention to the patient and observing and listening to the patient during the communication session, which can improve the patient's experience in receiving the care and recommendations provided by the care provider during the communication session.

In some embodiments, methods as well as a system or device for implementation of the method can be configured so that one or more of the following can occur during a communication session:
1. Patient health records stored on at least one computer device and/or electronic health record (EHR) system can be evaluated for reported conditions and/or medical codes.
2. Identified conditions can be associated with predetermined body regions.
3. Identified conditions can be prioritized and summarized.
4. Physiological landmarks in a video stream can be dynamically identified.
5. An indicator for one or more conditions of the patient can be overlaid on the patient's video to visually illustrate the presence of relevant health records or other information related to the patient's body that is displayed during the communication session to help guide the health care provider during a consultation that may occur during the communication session.
6. Multiple indicators can be included in the same video image during the video so that multiple indicators are simultaneously shown. The indicators can be shown differently (e.g. different colors, different color pattern and/or shading pattern, different sizing/shape, combinations thereof, etc.) to indicate the priority of the indicia based on a pre-selected priority criteria (e.g. age of record, severity of condition, prominence of the body part in the patient video stream being illustrated, etc.)

For example, a method for augmentation of patient data during a communication session is provided. In some embodiments, a method for augmentation of video of a patient during a communication session for display of an augmented video during the communication session can be provided. Embodiments of the method can include analyzing medical records stored in non-transitory memory to identify at least one patient condition of the patient during the communication session the at least one patient condition comprising diseases, injuries, medical codes and/or medical findings for the patient, associating the at least one patient condition identified based on the analyzing of the medical records with at least one body part of the patient, and generating medical record indicia for each of the at least one patient condition identified from the analyzing of the medical records. Each of the generated medical record indicia can be associated with a respective one of the at least one patient condition identified from the analyzing of the medical records and a medical record having the at least one patient condition identified from the analyzing of the medical records and the at least one body part of the patient associated with the at least one patient condition. The method can also include augmenting video data received from a patient device to overlay at least one medical record indicia on a body part of the patient included in the video data so that a graphical user interface (GUI) displayed via a care provider device shows the video with the generated medical record indicia shown over a portion of the body part of the patient associated with the at least one patient condition of the medical record associated with the medical record indicia. This display can occur during the communication session so that the care provider can see the medical record indicia during the communication session with the patient using the patient device.

In some embodiments, the association of the medical records with the patient condition can be performed by a first medical term parser device and the association of one or more patient body parts with the at least one identified patient condition can be performed via body part identification from the patient video data that is performed via at least one pose analyzer and the medical terms identified via the medical record parser. In some embodiments, the medical term parsing can be performed prior to a scheduled communication session with a particular patient. Then, during the communication session, the pose analyzing of patient body parts within the patient video stream can be evaluated during the session and associated with the medical terms and conditions identified via the medical parser's prior analysis of the patient's medical records. Such pre-communication session medical term parsing of relevant patient medical records can help speed up the generation and overlaying of the medical record indicia.

The method can also include other steps. For instance, the method can include displaying the medical record associated with the medical record indicia in response to selection of the medical record indicia and/or actuation of the medical record indicia during the communication session. Such selection or actuation can occur via a selection made using a touch screen display of the GUI or via use of a keyboard, button, or pointer device (e.g. mouse, stylus, etc.), for example.

Some embodiments of the method can be configured so that the care provider device or a communication session host device communicatively connected to the patient device and the care provider device performs the method. In other embodiments, the communication session host device can perform some steps of the method while other steps are performed by the care provider device or the patient device.

In some embodiments, the medical records can be stored in non-transitory memory of an electronic health record (EHR) device. In other embodiments, the records can be stored in other devices or in an EHR system as well as other devices of a healthcare provider system. In some embodiments, the method is performed by the care provider device and the care provider device is communicatively connected to the EHR device (e.g. an EHR device of an EHR system). In such embodiments, the GUI can be displayed on a display of the care provider device.

In some embodiments of the method, the communication session is a telehealth communication session between the patient device and the care provider device. Other embodiments may be designed so that the session is a dental health communication session or other type of health related communication session.

Embodiments of a communication apparatus are also provided. The apparatus can be configured as a communication system, a care provider device, or other type of communication apparatus. In some embodiments, the communication apparatus can include a computer device having a processor connected to a non-transitory memory. The computer device can have a medical term parser, a body part identifier, a pose analyzer, and/or a video annotator as well. In some embodiments, the computer device can also include a speech to text converter and context analyzer.

In some embodiments, the medical term parser can configure the computer device to analyze medical records stored in non-transitory memory of an electronic health record (EHR) device to identify at least one patient condition of a patient during a communication session. The at least one patient condition can include diseases, injuries, medical codes and/or medical findings for the patient; The body part identifier can configure the computer device to associate the at least one patient condition identified based on the analyzing of the medical records with at least one body part of the patient. The pose analyzer can configure the computer device to generate medical record indicia for each of the at least one patient condition identified from the analyzing of the medical records. Each generated medical record indicia can be associated with a respective one of the at least one patient condition identified from the analyzing of the medical records and a medical record having the at least one patient condition identified from the analyzing of the medical records and the at least one body part of the patient associated with the at least one patient condition. The video annotator can configure the computer device to augment video data received from a patient device of the patient to overlay at least one medical record indicia on a body part of the patient included in the video data so that a graphical user interface (GUI) is displayable to show the video with the generated medical record indicia shown over a portion of the body part of the patient associated with the at least one patient condition of the medical record associated with the medical record indicia during the communication session. The speech to text converter can convert audio data of the communication session into text. This transcribed text can be analyzed by a context analyzer to determine the context of the communication session. This context information can be utilized to help identify a relevancy of different medical record indicia to the communication session for use in illustration of the medical record indicia and/or for indication of the estimated relevancy of that indicia to the communication session.

The communication apparatus can include a number of different elements or be a single computer device. For instance, in some embodiments, the apparatus can be a care provider device, a communication session host device, or both devices communicatively connected to each other and communicatively connectable to a patient device. Some embodiments can also include other elements, such as the EHR device.

A non-transitory computer readable medium having an application stored thereon that defines a method performed by a computer device that runs the application is also provided. The method defined by the application can include analyzing medical records to identify at least one patient condition of the patient during a communication session. The at least one patient condition can include diseases, injuries, medical codes and/or medical findings for the patient. The method can also include associating the at least one patient condition identified based on the analyzing of the medical records with at least one body part of the patient and generating medical record indicia for each of the at least one patient condition identified from the analyzing of the medical records. Each generated medical record indicia can be associated with a respective one of the at least one patient condition identified from the analyzing of the medical records and a medical record having the at least one patient condition identified from the analyzing of the medical records and the at least one body part of the patient associated with the at least one patient condition. The method can also include augmenting video data received from a patient device to overlay at least one medical record indicia on a body part of the patient included in the video data so that a GUI is displayable to show video of the video data with the generated medical record indicia shown over a portion of the body part of the patient associated with the at least one patient condition of the medical record associated with the medical record indicia during the communication session.

The non-transitory computer readable medium can have an application stored thereon that defines a method to also include other elements. For instance, the method can also include displaying the medical record associated with the medical record indicia in response to selection of the medical record indicia and/or actuation of the medical record indicia during the communication session.

The computer device that can have the non-transitory computer readable medium or otherwise access that medium to run the application stored thereon can be a care provider device or a communication session host device communicatively connected to the patient device in some embodiments. Some embodiments can be configured so that the medical records that are analyzed are records that are stored on an EHR device communicatively connected to the computer device.

Other details, objects, and advantages of the telecommunications apparatus, system, device, non-transitory computer readable medium, and method will become apparent as the following description of certain exemplary embodiments thereof proceeds.

BRIEF DESCRIPTION OF THE DRAWINGS

The invention and embodiments thereof will be described below in further detail in connection with the drawings. It should be understood that like reference characters used in the drawings may identify like components.

DETAILED DESCRIPTION OF EXEMPLARY EMBODIMENTS

Figure 1:
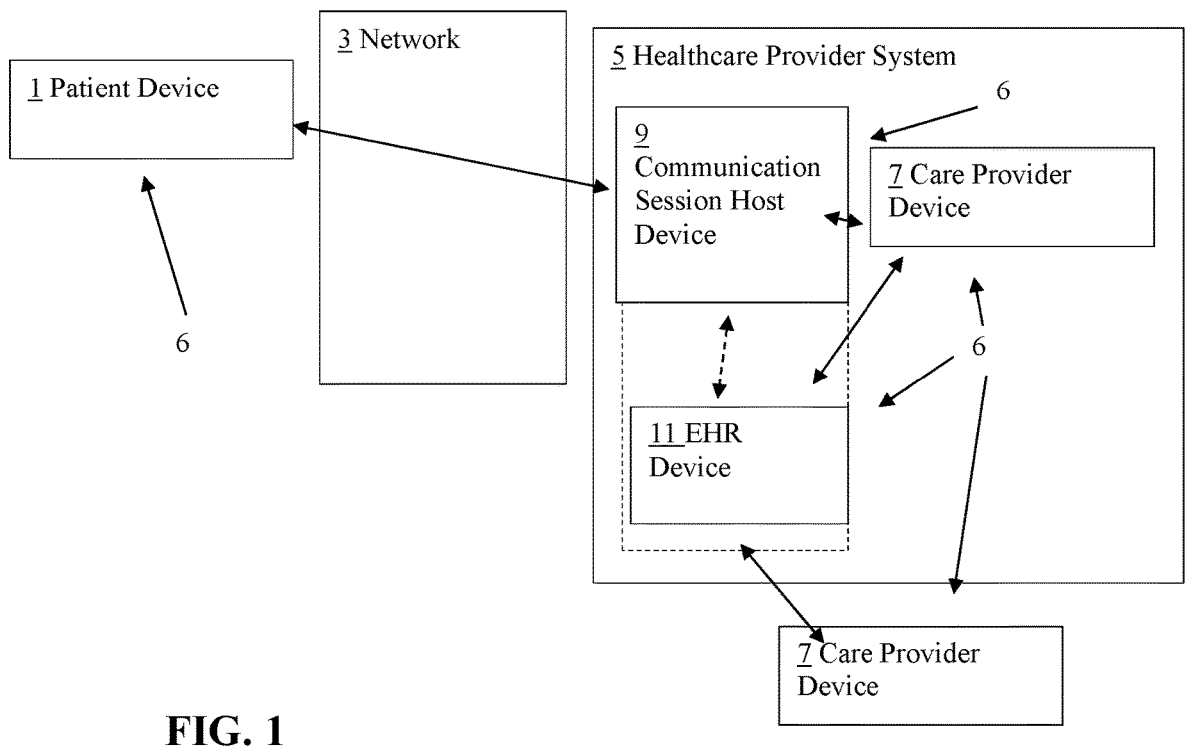
FIG. 1 is a block diagram of a first exemplary embodiment of a telecommunication apparatus.

Referring to FIGS. 1-7, a communication apparatus can include multiple computer devices 6 that can include a patient device 1 that can communicatively connect to at least one care provider device 7 via at least one network 3. The communication apparatus can also include a healthcare provider system 5 that includes a communication session host device 9 and an electronic health record (EHR) device 11. As indicated in broken line in FIG. 1, in some embodiments, the communication session host device 9 can be a device that includes the EHR device 11. In other embodiments, the communication session host device 9 can be separate from the EHR device 11 and be communicatively connectable to that device.

Figure 2:
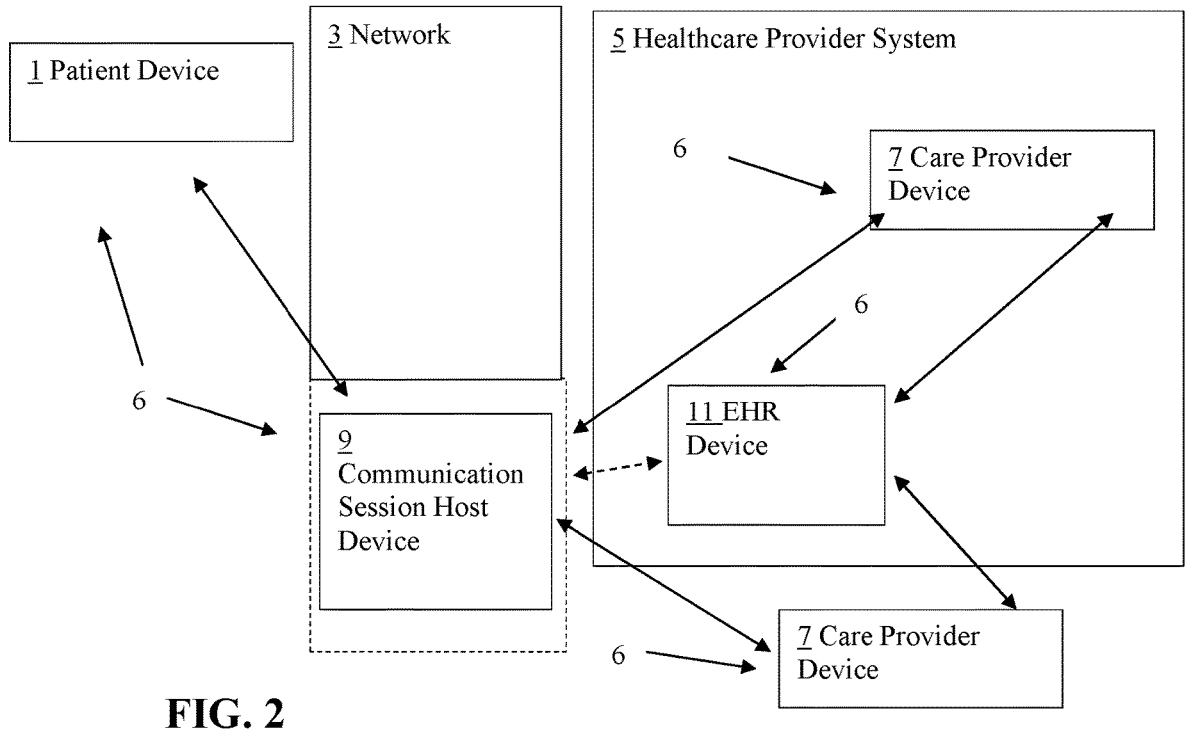
FIG. 2 is a block diagram of a second exemplary embodiment of a telecommunication apparatus.

The communication session host device 9 can be a component of the healthcare provider system 5 as shown in FIG. 1 or can be a device that is remote from this system that is communicatively connectable to an EHR device 11 of the healthcare provider system 5 via at least one network 3 as shown in FIG. 2. The communication session host device 9 can be within the network 3 as shown in broken line in FIG. 2 or can be communicatively connectable to the network 3 for a communication connection with the EHR device 11 and one or more care provider devices 7.

Care provider devices 7 can be within the healthcare provider system 5 or be remote from that system. In some embodiments, some of the care provider devices 7 are remote from the health care provider system 5 and others are within that system as shown in FIGS. 1 and 2. For example, the healthcare provider system 5 can include a healthcare provider network that includes multiple care provider devices 7 and also permits connection via a network connection or virtual network connection to other remote care provider devices 7. The care provider devices 7 can be communicatively connectable to each other and/or the patient device 1 via the communication session host device 9 as well as via other network connection mechanism that may facilitate such a communication connection. There can also be other network nodes that can facilitate communications between the devices, such as, for example, routers, access points, gateways, base stations, border control devices, or other node devices.

Figure 3:
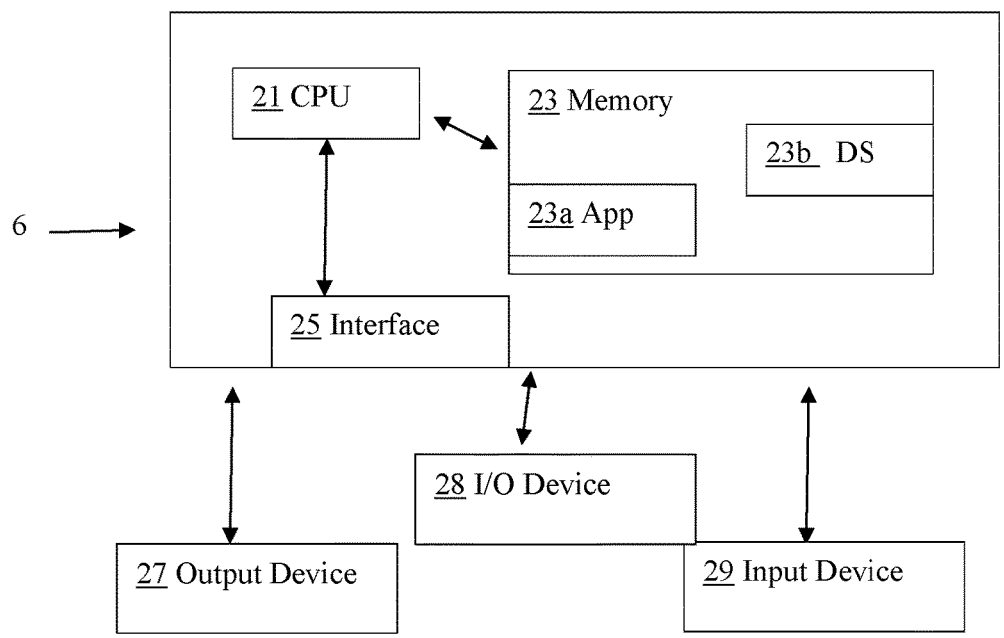
FIG. 3 is a block diagram illustrating exemplary elements of exemplary communication devices 6.

As may be appreciated from FIG. 3, each of the computer devices 6 can be configured as a communication device (e.g. a server, a communication terminal such as a laptop computer, smart phone, tablet, desktop computer, a document management server or database server, etc.) For example, the EHR device 11 can be a server or computer system configured to store health records for a number of patients, the communication session host device 9 can be a server or other device that can host communication services between multiple communication terminals such as a patient device 1 and at least one care provider device 7, and the patient device 7 and care provider device 7 can each be a communication terminal, such as, for example, a smart phone, tablet, laptop computer, or personal computer.

Each computer device 6 can include a processor, such as CPU 21 shown in FIG. 3. The processor can be a hardware processor that can be a core processor, microprocessor, central processing unit, array of interconnected processors, or other type of processor. The processor can be connected to non-transitory memory 23 and at least one interface 25 that can facilitate communication connections with other devices or networks. The one or more interfaces 25 can include a network connection interface, a cellular network connection interface, a wireless network connection interface, and at least one near filed connection interface (e.g. a Bluetooth connection interface, etc.) The memory 23 can be flash memory, a hard drive, a solid state drive, or other type of non-transitory computer readable medium. The memory 23 can store at least one application ("App"), such as at least one App 23a, and can also store one or more other data stores 23b, such as a data store, DS. One or more input/output (I/O) devices 28, output devices 27, and/or input devices 29 can be communicatively connected to the processor 21. These I/O deices 28 can include a touchscreen for example. The output devices 27 can include a display, a monitor, a printer, and/or a speaker. The input devices 29 can include a microphone, a camera, a keyboard, a pointer device (e.g. a mouse or a stylus), a keypad, buttons, at least one motion sensor, or other type of input device 29. The input devices, I/O devices, and output devices can be connected to the processor 21 via a wireless connection (e.g. a Bluetooth connection) or a wired connection (e.g. a universal serial bus ("USB") connection, etc.).

The communication session host device 9 can be configured to facilitate a communication session between a patient device 1 and at least one care provider device 7 (e.g. a care provider device 7 of a doctor or surgeon). The communication session host device 9 can receive video and audio data for the communication session from each device, mix the data, and provide the data to the devices during the communication session to facilitate a video communication session. The communication session can be supported so that a video obtained via a camera of each communication session participant's terminal device is provide to the communication session host device along with audio data recorded by the microphone of that participant's terminal device for mixing of the data and providing the mixed data to the participants' devices for output of audio of the communication session as well as the video data of the devices. For example, a patient device 1 can provide video and audio data to the communication session host that can then process that data and provide augmented video data and the audio data to the care provider device 7 during the session. The communication session host device 9 can also receive video data and/or audio data from the care provider device and provide that data to the patient device. The data can be conveyed via the communication session host device 9 so a video can be displayed on each terminal device showing the recorded video of the other communication session participant. For instance, the video recorded by the care provider device can be output on a display of the patient device and the video recorded by the patient device 1 can be output on a display of the patient device.

Figure 5:
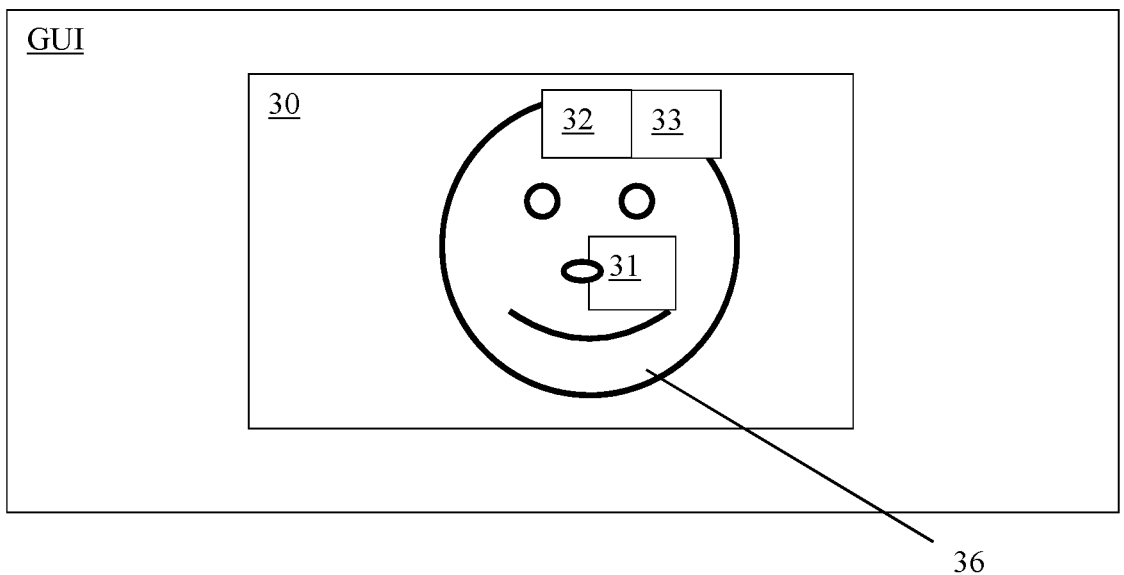
FIG. 5 is a block diagram illustrating a first exemplary GUI display.
Figure 6:
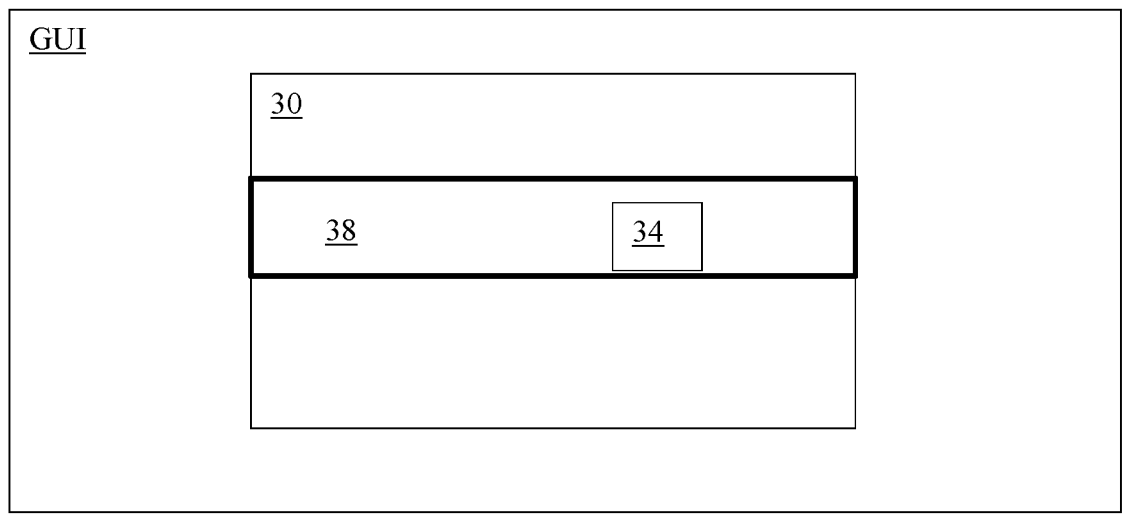
FIG. 6 is a block diagram illustrating a second exemplary GUI display.

FIGS. 5 and 6 illustrate an exemplary graphical user interface (GUI) illustrating video recorded by the patient device 1 that can be augmented and subsequently sent by the communication session host device 9 to the care provider device 7 or that can be augmented by the care provider device 7 for display at the care provider device 7 via an output device 27 or I/O device 28 of the care provider device 7. The video displayed at the care provider device 7 can include video recorded by the patient device 1 that includes an image of at least one patient body part (e.g. head 36 or leg 38) along with indicia, such as medical record indicia 31, 32, 33, and 34, that is overlaid onto the images displayed at the care provider device's output device 27 or I/O device 28. The indicia can be provided to augment the recorded patient video so that the indicia is displayed in an overlaid position on the body part(s) of the patient shown in the displayed GUI to quickly identify relevant medical records related to the displayed body part(s). The care provider can provide input via an input device 29 or the I/O device 28 (e.g. touching the screen location having an indicia, selecting an indicia via a pointer device, etc.) to select the indicia and actuate it so that the medical record associated with the indicia is displayed in the GUI or in a separate window that opens on a display of the care provider device 7.

The care provider can choose to review that record via his or her care provider device 7 while the patient is talking during the communication session or otherwise perform the review during the communication session. This can occur without the patient knowing the care provider has opened and reviewed the record. The care provider can also utilize a share screen function to show the record being reviewed to the patient during the communication session as well. In the event the share screen function is actuated via input provided by use of the GUI, the communication session host device 9 can receive the data related to the shown medical record displayed at the care provider device 7 and provide that data to the patient device 1 so that the patient device 1 can also display the displayed medical record during the communication session.

Figure 4:
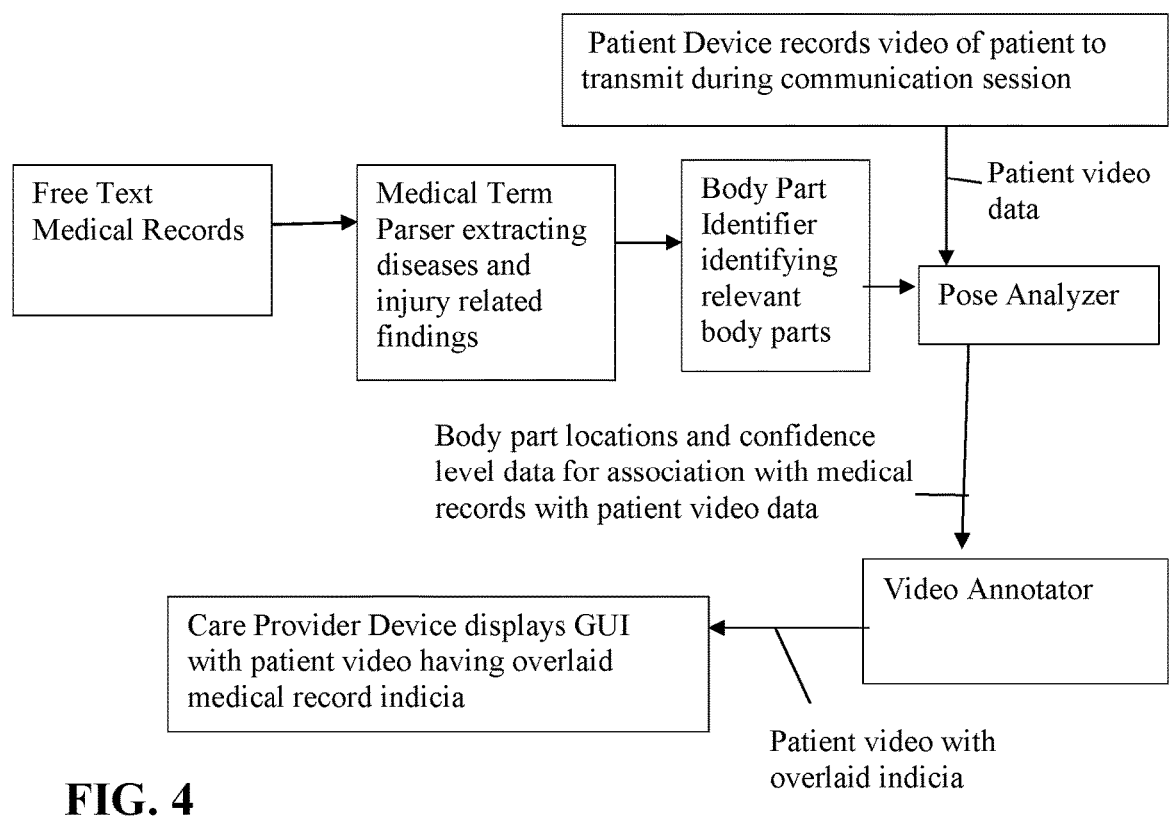
FIG. 4 is a flow chart illustrating an exemplary process for augmenting video data received from a patient device and providing it for display via a graphical user interface (GUI) displayed via a care provider device.

FIG. 4 illustrates an exemplary process for generation of indicia for overlaying the indicia (e.g. medical record indicia 31-34) onto the patient's recorded video for display in a GUI shown at output device 27 or I/O device 28 of the care provider device 7 (e.g. shown via touch screen or display of the care provider device). The communication session host device 9 or the care provider device 7 can be configured to utilize this process or another embodiment of this process. For instance, an application (e.g. App 23a) defining the process can be stored in memory 23 of the communication session host device 9 or the care provider device 7 that includes instructions that define this process to be performed by the device when the device's processor 21 runs the application.

In some embodiments, this indicia overlay process can include: (1) mining patient medical records from the EHR device 11 for reported conditions and/or medical codes associated with reported conditions of the patient; (2) associating conditions identified from the mined patient medical records with pre-determined body regions (e.g. hand, face, foot, leg, arm, chest, back, nose, ear, cheek, eye, forehead, forearm, shin, thigh, buttocks, lower back, mid back, upper back, shoulder, right hand, left hand, left foot, right foot, etc.); (3) prioritizing and summarizing the conditions identified from the medical records; (4) dynamically identifying physiological landmarks in video data received from a patient device (e.g. a video feed of the patient device providing video recorded at the patient device, etc.); and (5) overlaying at least one indicia for an identified condition on the patient's video data to visually identify the presence of the medical record to the care provider to help guide the care provider during a consultation that may occur in the communication session. To mine the medical records, the communication session host device 9 or care provider device 7 can perform searches of medical records stored at the EHR device 11 or communication with the EHR device to receive copies or access to the patient's records to perform the searching for relevant records. Audio data received by the communication session host device 9 or the care provider device 7 can be utilized to identify key terms and utilize those terms to prioritize record searching and indicia overlaying functions as well.

In some embodiments, the communication session host device 9 or care provider device 7 can include different elements to provide the medical record indicia overlay functionality. These functions can be different units of the device or can be different components of an App. or different programs called for in the App. to provide these functions. For instance, the communication session host device 9 or the care provider device 7 can include a medical term parser, a body part identifier, a pose analyzer, and a video annotator as shown in FIG. 4.

In some embodiments, the medical term parser can configure the computer device 6 (e.g. care provider device 7 or communication session host device 9) to analyze medical records stored in non-transitory memory of the EHR device 11 to identify at least one patient condition of a patient during a communication session. The at least one patient condition can include diseases, injuries, medical codes and/or medical findings for the patient. The body part identifier can configure the computer device 6 to associate at least one patient condition identified based on the analyzing of the medical records with at least one body part of the patient. The pose analyzer can configure the computer device 6 to generate medical record indicia for each patient condition identified from the analyzing of the medical records. Each generated medical record indicia can be associated with (1) a respective patient condition identified from the analyzing of the medical records, (2) a medical record having the patient condition identified from the analyzing of the medical records and (3) at least one body part of the patient associated with the patient condition. The video annotator can configure the computer device 6 to augment video data received from the patient device 1 of the patient to overlay at least one medical record indicia on a body part of the patient included in the video data so that a graphical user interface (GUI) is displayable to show the video with the generated medical record indicia shown over a portion of the body part of the patient associated with the patient condition of the medical record associated with the medical record indicia during the communication session.

For example, the medical term parser can analyze patient records of the patient using a patient identifier the patient device 1 or care provider device 7 may have provided to the communication session host device 9. The medical term parser can review the records for reported medical conditions and/or medical codes associated with different conditions. The identified conditions can then be utilized by the body part identifier to associated different identified conditions with relevant body parts of the patient (e.g. a concussion is associated with the patient's head, a broken right forearm is associated with the patient's right forearm, a torn knee ligament is associated with the patients' knee, a sprained left ankle is associated with the patient's left ankle, etc.). The terms for the different patient conditions and body parts associated with those conditions can then be utilized by the pose analyzer to identify body part locations shown in the patient video data and identify locations on which indicia should be positioned to overlay the body parts associated with the different conditions identified from the analyzed medical records. This body apart location data can include confidence level data that indicates the degree of certainty that a particular record may be associated with a particular patient body part. This data is utilize by the video analyzer to augment the patient video so that medical record indicia is overlaid on locations of the patient's body that is shown in the video so that this indicia is output in a GUI shown to the care provider using the care provider device 7 during the communication session.

In some embodiments, the association of the medical records with the patient condition can be performed by a first medical term parser device and the association of one or more patient body parts with the at least one identified patient condition can be performed via body part identification from the patient video data that is performed via at least one pose analyzer and the medical terms identified via the medical record parser. In some embodiments, the medical term parsing can be performed prior to a scheduled communication session with a particular patient. Then, during the communication session, the pose analyzing of patient body parts within the patient video stream can be evaluated during the session and associated with the medical terms and conditions identified via the medical parser's prior analysis of the patient's medical records. Such pre-communication session medical term parsing of relevant patient medical records can help speed up the generation and overlaying of the medical record indicia.

The medical record indicia can be generated to have different colors or other visual markers to indicate the potential relevance of the identified medical record associated with the displayed indicia. For instance, records that are older than a pre-selected age threshold can have a first color indicating that the records are older than more recent records that are within or under the age threshold. As another example, the indicia can include an icon shape or other marker to indicate the confidence level for the relevancy and/or accuracy of location for the displayed indicia. As yet another example, how each indicia is displayed can be adjusted to visually convey the relevance of a particular record associated with the displayed indicia based on the context of the audio exchanged during the communication session by illustrating some indicia related to named body parts in a pre-selected primary indicator color that differs from a non-primary indicator color that other non-contextually relevant indicia may have (e.g. if a hand is discussed during the session, indicia on a patient hand can be shown in a primary indicator color while indicia on a head or leg may be shown in a non-primary indicator color). The relevancy of a particular indicia can be based on the context of the communication session, which can include content of the audio exchanged during the communication session, body parts displayed in the patient video during the session, and/or age of the record associated with the indicia.

In some embodiments, the medical term parser can be configured as a natural language processing (NLP) parser that is capable of negation and uncertainty detection. For example, the utilization of negation functionality can be helpful in assessing medical records as text related to no sign of disease or no sign of injury can be relevant to the evaluation of a medical record and its relevance to a particular communication session. Input into the medical term parser can include records from the EHR device 11 and the output from the medical term parser can include list of identified diseases, injuries, medical codes (e.g. code 381.10 for otitis, which should be mapped as corresponding to the patient's ear, etc.) and/or medical findings.

The body part identifier can be table driven and not hard coded (or alternatively can be hard coded). The body part identifier can be configured to frequent updates and configured to fetch data related to terms and medical codes from a central repository for updating the body part identifier. The body part identifier can be configured to utilize the list obtained from the medical term parser and translate the data so body parts corresponding to the conditions in the medical term parser list can be identified (e.g. ear can be identified for an otitis condition identified in the list so that the patient's ear is identified as corresponding to the otitis record).

The pose analyzer can be a real-time pose analyzer such as a neural network-based pose analyzer or a device dominant pose analyzer. The pose analyzer can be configured to detect the body parts of a patient in the patient video data recorded by the patient device and identify locations for different body parts that are indicated as having associated records via the body part identifier and patient body recorded in the patient video data. The input to the pose analyzer can include real-time video data received from the patient device. The output for the pose analyzer can be the video stream with an overlay or indicia overlay data for indicia overlay positioning if any indicia for relevant records was identified for any body parts shown included in the video stream.

The video annotator can be configured to combine the outputs from the medical term parser and pose analyzer to annotate the video for the care provider. The video annotator can utilize information obtained via the medical term parser, body part identifier, and pose analyzer to provide indicia data for the location of indicia and how the indicia are displayed so the indicia is displayed in a GUI shown on a display device of the care provider device 7 in locations that overlay corresponding relevant body parts of the patient so that indicia associated with records related to a particular body part are overlaid on or adjacent that body part in the video shown in the care provider device GUI during the communication session (e.g. in real-time during the session).

The location for indicia at different patient body parts and size of the indicia can be selected based on the resolution and size of the body parts within the video data. In some embodiments, the poser analyzer that is utilized for a particular communication session can depend on the device capabilities running the application so that the processing and power consumption requirements for the pose analyzer are suitable for the particular device running the analyzer. In some embodiments where the device running the application has sufficient processing capacity and power utilization, multiple different pose analyzers can be run at the same time to perform the pose analysis functions for providing improved accuracy and body part identification for locating the indicia positions for overlaying of the medical record indicia.

The computer device 6 can be configured so that the pose analyzer that is run can be selected based on the prominence of a body part illustrated in the recorded patient video stream that is transmitted by the patient device 1. For instance, when the patient shows the hand to the camera of the patient device 1 to have the patient hand be the most prominent part of the body shown in the video stream transmitted to the care provider device 7 during the communication session, a pose analyzer can be selected that identifies fine details of a hand as compared to a pose analyzer that is more specifically configured for identifying fine details of a leg, chest, back, arm, or head. As another example, a computer device 6 can have multiple pose analyzers that are each more specifically configured for a particular human body part or region of a human body (e.g. is configured to provide finer, or more detailed, identification of different features of a human body within a pre-selected region of the body) so that a particular one of those pose analyzers is selected based on which patient body part has the greatest prominence in the video stream (e.g. takes up the most space or surface area on the recorded video image, takes up the most area within the recorded video frame of the video stream, etc.). The pose analyzer in such embodiments can be selected after the body part prominence detection occurs by the computer device 6.

The computer device 6 can also include a speech to text converter to convert audio data of the communication session into text. This transcribed text can then be analyzed by a context analyzer to determine the context of the communication session. This context information can be utilized to help identify a relevancy of different medical record indicia to the communication session for use in illustration of the medical record indicia and/or for displaying the medical record indicia for indication of the estimated relevancy of that indicia to the communication session (e.g. use of different colors, shading pattern, or other relevancy display indicator for the estimated relevancy of the displayed medical record indicia to the topic(s) being discussed in the communication session).

In the exemplary GUI shown in FIG. 5, a care provider device's GUI can show a patient's video that includes multiple medical record indicia positioned over different body parts of the patient (e.g. nose and forehead of the patient body shown in the video recorded by the patient device for display at the care provider device). Each medical record indicia can be overlaid on the real-time live video stream received from the patient device 1 so that the care provider can be recorded by the camera of the care provider device 7 as maintain eye contact with the patient's video shown on his or her GUI while reviewing the medical record indicia or medical records displayed in response to selection or actuation of the medical record indicia. How the medical record indicia is displayed can be tailored to the context of the communication session that is determined from audio of the communication session (e.g. via an analysis of the text that was converted based on a speech to text conversion of the audio data transmitted during the communication session, detection of the prominence of a particular body part shown in the patient video, etc.).

In a situation where the communication session results in the body parts shown in the video feed from the patient changing (e.g. the video illustrates the patient's leg 38 instead of his or her head 36), the body parts can be analyzed via the pose analyzer for generation of medical record indicia associated with those new body parts. Any new or additional indicia can then be augmented into the patient video by overlaying any new medical record indicia for the newly shown body part on the care provider GUI. The generated indicia can be overlaid so that the medical record indicia follows the patient body part to which it is associated during the video stream of the patient shown in the care provider device's GUI so that the medical record indicia stays positioned over the moving patient body party during the communication session. Such continuous positional adjustment can permit the medical record indicia to keep the context of the medical record and its association with the shown patient body part illustrated in the patient's video displayed on the care provider device's GUI throughout the communication session.

As yet another example, in a situation during the communication session where the patient shows a particular body part (e.g. patient's hand, arm, back, leg, etc.), the newly shown body part recorded in the patent device video data can be analyzed via the pose analyzer and any new medical record indicia for any condition or record related to that newly shown part can be generated for being overlaid onto the newly illustrated body part. The care provider can actuate any medical record indicia by use of an input device 29 or I/O device 28 of the care provider device 7 to have the medical record associated with the selected or actuated medical record indicia displayed during the session. In embodiments in which the care provider device has multiple displays, one display may display the GUI having the patient recorded via with medical record indicia overlaid thereon while the second display may illustrate one or more of the medical records associated with the indicia that were selected or otherwise actuated by the care provider during the communication session.

Figure 7:
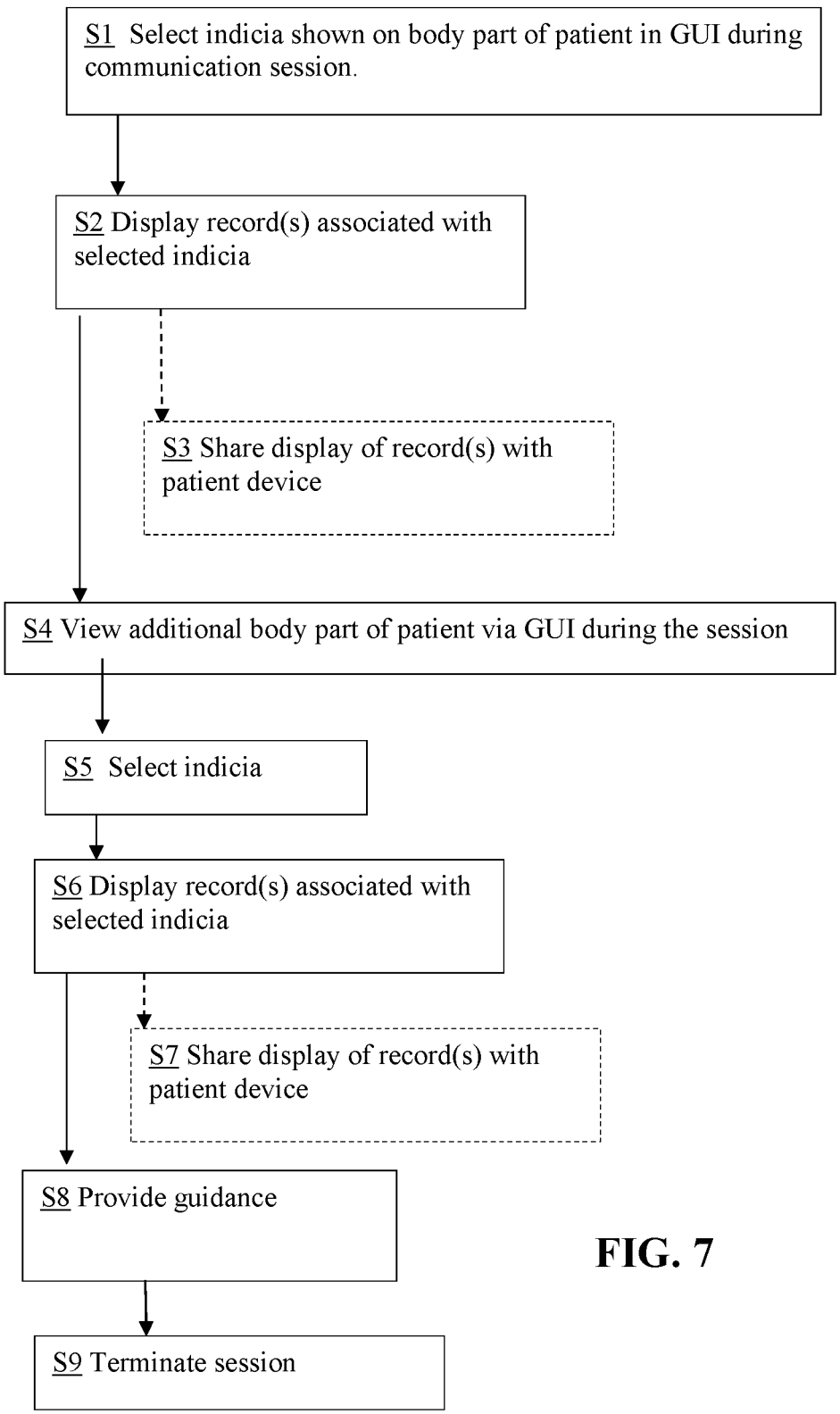
FIG. 7 is a flow chart illustrating an exemplary method for utilizing exemplary medical record indicia overlaid on a patient video on a health care provider GUI displayed on a care provider device's display.

As another example, FIG. 7 illustrates an exemplary process in which medical record indicia that is generated and shown in a GUI during a communication session can be utilized to provide care during a telehealth communication session utilizing an embodiment of the computer apparatus such as, for examples, the different embodiments shown in FIGS. 1-6 and discussed above. For example, medical record indicia that was generated and shown in a GUI of a care provider device 7 as being overlaid on a part of a patient body within video of the patient received from the patient device 1 of the patient can be selected in a first step S1 during the communication session. The record(s) associated with that indicia can then be displayed in response to that selection in a step S2. The display of the record can optionally be shared during the session in an optional step S3 (shown in broken line). A new patient body part may be shown in the care provider GUI during the communication session at a later time in a step S4. Medical record indicia can be generated and overlaid onto the body part of the patient shown in the GUI as discussed herein for the newly shown body part. The medical record indicia related to that newly shown body part can be selected in a step S5 and the record(s) associated with that selected indicia can be displayed in response to that selection in a step S6. The displayed record or records can optionally be shared so it is also viewable by the patient via the patient device's GUI during the session in an optional step S7 (shown in broken line). The care provider may then provide guidance during the communication session related to the discussion of medical issues that occurred in the communication session and the review of the pertinent medical records reviewed via actuation of the different medical record indicia during the communication session in a step S8. The communication session may then be terminated after the guidance or care is provided.

The generated medical record indicia and overlaying of that indicia that can be provided by embodiments of our invention can help speed up a consultation a patient may have with a care provider, such as a doctor, during a telecommunications communication session (e.g. a telehealth session, etc.) as a care provider can be automatically shown indicia for relevant medical history information and then quickly obtain that information during a communication session. The display of the overlaid medical record indicia can also help improve the patient's experience during a consultation as a care provider can maintain eye contact with a patient during the communication session by looking at the care provider device camera recording the care provider during the session while the care provider may be reviewing relevant records via actuation of the indicia and subsequent display of those records during the communication session. The patient's perception of the consultation can be improved by having the perception of dedicated attention from the care provider even while that care provider is reviewing relevant records during the communication session.

It should be appreciated that different embodiments of the method, system, and apparatus can be developed to meet different sets of design criteria. For example, the particular type of network connection, server configuration or client configuration for a device for use in embodiments of the method can be adapted to account for different sets of design criteria. As yet another example, it is contemplated that a particular feature described, either individually or as part of an embodiment, can be combined with other individually described features, or parts of other embodiments. The elements and acts of the various embodiments described herein can therefore be combined to provide further embodiments. Thus, while certain exemplary embodiments of a telecommunication apparatus, telecommunication device, terminal device, a network, a server, a communication system, and methods of making and using the same have been shown and described above, it is to be distinctly understood that the invention is not limited thereto but may be otherwise variously embodied and practiced within the scope of the following claims.

What is claimed is:

1. A method for augmentation of video of a patient during a communication session for display of an augmented video during the communication session comprising:
   analyzing medical records stored in non-transitory memory to identify at least one patient condition of the patient during the communication session, the at least one patient condition comprising diseases, injuries, medical codes or medical findings for the patient;
   associating the at least one patient condition identified based on the analyzing of the medical records with at least one body part of the patient;
   generating medical record indicia for each of the at least one patient condition identified from the analyzing of the medical records, each generated medical record indicia associated with a respective one of the at least one patient condition identified from the analyzing of the medical records and a medical record having the at least one patient condition identified from the analyzing of the medical records and the at least one body part of the patient associated with the at least one patient condition;
   augmenting video data received from a patient device to overlay at least one medical record indicia on a body part of the patient included in the video data so that a graphical user interface (GUI) displayed via a care provider device shows video with the generated medical record indicia shown over a portion of the body part of the patient associated with the at least one patient condition of the medical record associated with the medical record indicia during the communication session;
   selecting a pose analyzer to analyze the body part of the patient included in the video data based on a prominence of the body part for performing the augmenting of the video data to overlay at least one medical record indicia on the body part, the medical record indicia including a plurality of medical record indicia that have at least two of: different coloration, different shading pattern, different sizes, and different shapes to indicate an estimated relevancy of the medical record indicia to a topic being discussed in the communication session.

2. The method of claim 1, wherein the method also comprising:
   displaying the medical record associated with the medical record indicia in response to selection of the medical record indicia or actuation of the medical record indicia during the communication session.

3. The method of claim 1, wherein the care provider device or a communication session host device communicatively connected to the patient device and the care provider device performs the method.

4. The method of claim 1, wherein the medical records are stored in non-transitory memory of an electronic health record (EHR) device.

5. The method of claim 4, wherein the method is performed by the care provider device, the care provider device communicatively connected to the EHR device.

6. The method of claim 5, wherein the GUI is displayed on a display of the care provider device.

7. The method of claim 1, wherein the communication session is a telehealth communication session between the patient device and the care provider device.

8. A communication apparatus comprising:
a computer device having a processor connected to a non-transitory memory; and
the computer device having a medical term parser, a body part identifier, a pose analyzer, and a video annotator; and
wherein:
the medical term parser configures the computer device to analyze medical records stored in non-transitory memory of an electronic health record (EHR) device to identify at least one patient condition of a patient during a communication session involving a patient device of the patient, the at least one patient condition comprising diseases, injuries, medical codes or medical findings for the patient;
the body part identifier configures the computer device to associate the at least one patient condition identified based on the analyzing of the medical records with at least one body part of the patient;
the pose analyzer configures the computer device to generate medical record indicia for each of the at least one patient condition identified from the analyzing of the medical records, each generated medical record indicia associated with a respective one of the at least one patient condition identified from the analyzing of the medical records and a medical record having the at least one patient condition identified from the analyzing of the medical records and the at least one body part of the patient associated with the at least one patient condition; and
the video annotator configures the computer device to augment video data received from the patient device of the patient to overlay at least one medical record indicia on a body part of the patient included in the video data so that a graphical user interface is displayable to show video of the video data with the generated medical record indicia shown over a portion of the body part of the patient associated with the at least one patient condition of the medical record associated with the medical record indicia during the communication session; and
wherein the pose analyzer configures the computer device to analyze the body part of the patient included in the video data based on a prominence of the body part for the augmentation of the video data to overlay at least one medical record indicia on the body part, the medical record indicia including a plurality of medical record indicia that have at least two of: different coloration, different shading pattern, different sizes, and different shapes to indicate an estimated relevancy of the medical record indicia to a topic being discussed in the communication session.

9. The communication apparatus of claim 8, including the EHR device.

10. The communication apparatus of claim 9, wherein the computer device is a communication session host device or a care provider device.

11. A non-transitory computer readable medium having an application stored thereon that defines a method performed by a computer device that runs the application, the method comprising:
analyzing medical records to identify at least one patient condition of the patient during a communication session, the at least one patient condition comprising diseases, injuries, medical codes or medical findings for the patient;
associating the at least one patient condition identified based on the analyzing of the medical records with at least one body part of the patient;
generating medical record indicia for each of the at least one patient condition identified from the analyzing of the medical records, each generated medical record indicia associated with a respective one of the at least one patient condition identified from the analyzing of the medical records and a medical record having the at least one patient condition identified from the analyzing of the medical records and the at least one body part of the patient associated with the at least one patient condition;
augmenting video data received from a patient device to overlay at least one medical record indicia on a body part of the patient included in the video data so that a graphical user interface is displayable to show video of the video data with the generated medical record indicia shown over a portion of the body part of the patient associated with the at least one patient condition of the medical record associated with the medical record indicia during the communication session;
selecting a pose analyzer to analyze the body part of the patient included in the video data based on a prominence of the body part for performing the augmenting of the video data to overlay at least one medical record indicia on the body part, the medical record indicia including a plurality of medical record indicia that have at least two of: different coloration, different shading pattern, different sizes, and different shapes to indicate an estimated relevancy of the medical record indicia to a topic being discussed in the communication session.

12. The non-transitory computer readable medium of claim 11, wherein the method also comprising:
displaying the medical record associated with the medical record indicia in response to selection of the medical record indicia or actuation of the medical record indicia during the communication session.

13. The non-transitory computer readable medium of claim 11, wherein the computer device is a care provider device or a communication session host device communicatively connected to the patient device.

14. The non-transitory computer readable medium of claim 11, wherein the medical records are stored on an electronic health record (EHR) device communicatively connected to the computer device.

15. The non-transitory computer readable medium of claim 11, wherein the medical record indicia is generated to visually differentiate medical records by one or more of: age and relevance to a context of the communication session.

16. The non-transitory computer readable medium of claim 11, wherein the video data received from the patient device is video of the patient recorded by a camera of the patient device during the communication session that is transmitted to a communication session host device during the communication session.

17. The method of claim 1, wherein the video data received from the patient device is video of the patient recorded by a camera of the patient device during the communication session that is transmitted to a communication session host device during the communication session.

* * * * *